(12) United States Patent
McLuckey et al.

(10) Patent No.: US 7,550,718 B2
(45) Date of Patent: Jun. 23, 2009

(54) PROCESS FOR INCREASING IONIC CHARGE IN MASS SPECTROMETRY

(75) Inventors: Scott A. McLuckey, West Lafayette, IN (US); Min He, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 304 days.

(21) Appl. No.: 10/558,610

(22) PCT Filed: May 30, 2003

(86) PCT No.: PCT/US03/17022

§ 371 (c)(1),
(2), (4) Date: Nov. 29, 2005

(87) PCT Pub. No.: WO2004/109274

PCT Pub. Date: Dec. 16, 2004

(65) Prior Publication Data

US 2007/0015158 A1    Jan. 18, 2007

(51) Int. Cl.
   *B01D 59/44* (2006.01)
(52) U.S. Cl. .......................... 250/282; 250/292; 435/6
(58) Field of Classification Search ................. 250/282
   See application file for complete search history.

(56) References Cited

U.S. PATENT DOCUMENTS

| 4,849,628 | A | 7/1989 | McLuckey et al. |
| 6,087,658 | A | 7/2000 | Kawato |
| 6,373,051 | B1 * | 4/2002 | Hayakawa et al. ........... 250/282 |
| 7,084,396 | B2 * | 8/2006 | Schneider ................... 250/288 |

2003/0155502 A1 * 8/2003 Grosshans et al. .......... 250/282

OTHER PUBLICATIONS

R. E. March et al., "Practical Aspects of Ion Trap Mass Spectrometry", vol. I—Fundamentals of Ion Trap Mass Spectrometry, Chapter 2—Theory of Quadrupole Mass Spectrometry, *CRC Press*, 1995, pp. 25-48.
R. E. March et al., "Practical Aspects of Ion Trap Mass Spectrometry", vol. I—Fundamentals of Ion Trap Mass Spectrometry, Chapter 3—Nonlinear Ion Traps, *CRC Press*, 1995, pp. 49-167.
R. E. March et al., "Practical Aspects of Ion Trap Mass Spectrometry", vol. I—Fundamentals of Ion Trap Mass Spectrometry, Chapter 4—Commercialization of the Quadrupole Ion Trap, *CRC Press*, 1995, pp. 169-205.
R. E. March et al., "Practical Aspects of Ion Trap Mass Spectrometry", vol. II—Ion Trap Instrumentation, Chapter 1—High Mass, High Resolution Mass Spectrometry, *CRC Press*, 1995, pp. 3-47.
R. E. March et al., "Practical Aspects of Ion Trap Mass Spectrometry", vol. II—Ion Trap Instrumentation, Chapter3—Electrospray and the Quadrupole Ion Trap, *CRC Press*, 1995, pp. 89-141.

(Continued)

*Primary Examiner*—Nikita Wells
*Assistant Examiner*—Phillip A. Johnston
(74) *Attorney, Agent, or Firm*—Barnes & Thornburg LLP (57) ABSTRACT

Processes and apparatus are described for the analysis of molecules or fragments thereof, which are capable of carrying multiple charges, by reacting the multiply charged molecules or fragments thereof with other ions using mass spectrometry.

32 Claims, 5 Drawing Sheets

OTHER PUBLICATIONS

R. R. O. Loo et al., "A New Approach for the Study of Gas-Phase Ion-Ion Reactions Using Electrospray Ionization", *J. Am Soc. Mass Spectrom*, 1992, vol. 3, pp. 695-705.

J. L. Stephenson, Jr. et al.; "Anion Effects on Storage and Resonance Ejection of High Mass-to-Charge Cations in Quadrupole Ion Trap Mass Spectrometry," Anal. Chem. 69: 3760-3766; 1997.

S. J. Gaskell, "Electrospray: Principles and Practice", *Journal of Mass Spectrometry*, 1997, vol. 32, pp. 677-688.

J. F. Mahoney et al., "Massive Cluster Impact Mass Spectrometry: A New Desorption Method for the Analysis of Large Biomolecules", *Rapid Commun. Mass Spectrom*, 1991, vol. 5, pp. 441-445.

A.G. Marshall et al.; "Fourier Transform Ion Cyclotron Resonance Mass Spectrometry: A Primer," Mass Spectromety Reviews, 17: 1-35, 1999.

B. A. Collings et al.; "A combined linear ion trap time-of flight system with improved performance and $MS^n$ capabilities," Rapid Commun. Mass Spectrom., 15: 1777-1795, 2001.

J. M. Campbell et al.: "A New Linear Ion Trap Time-of-flight System with Tandem Mass Spectrometry Capabilities," Rapid Commun. Mass Spectrom., 12: 1463-1474, 1998.

J. L. Stephenson, Jr. et al., Adaptation of the Paul Trap for study of the reaction of multiply charged cations with singly charged anions, *Int J Mass Spectrom & Ion Processes* 1997, vol. 162, pp. 89-106.

D. E. Clemmer et al., "Ion Mobility Measurements and their Applications to Clusters and Biomolecules", *Journal of Mass Spectrometry*, 1997, vol. 32, pp. 577-592.

R. D. Smith et al., "Trapping, detection and reaction of very large single molecular ions by mass spectrometry", *Nature*, 1994, vol. 369, pp. 137-139.

S. A. McLuckey et al., "Ion/Molecule Reactions for Improved Effective Mass Resolution in Electrospray Mass Spectrometry", *Anal. Chem.*, 1995, vol. 67, No. 14, pp. 2493-2497.

J. M. Wells et al., "Charge dependence protonated insulin decompositions", *International Journal of Mass Spectrometry*, 2000, vol. 203, pp. 1-9.

W. J. Herron et al., "Ion-Ion Reactions in the Gas Phase: Proton Transfer Reactions of Protonated Pyridine with Multiply Charged Oligonucleotide Anions", *J. Am. Soc. Mass Spectrom*, 1995, vol. 6, pp. 529-532.

A. P. Hunter et al., "Proton-transfer Reactions of Mass-selected Multiply Charged Ions", *Rapid Communications in Mass Spectrometry*, 1994, vol. 8, pp. 417-422.

S. A. McLuckey et al., "Novel quadrupole ion trap methods for characterizing the chemistry of gaseous macro-ions", *International Journal of Mass Spectrometry*, 2000, vol. 200, pp. 137-161.

J. L. Stephenson, Jr., et al., "Gaseous Protein Cations Are Amphoteric", *J. Am. Chem. Soc.*, 1997, vol. 119, No. 7, pp. 1688-1696.

S. A. McLuckey et al., "Ion/Ion Proton-Transfer Kinetics: Implications for Analysis of Ions Derived from Electrospray of Protein Mixtures", *Anal. Chem.*, 1998, vol. 70, No. 6, pp. 1198-1202.

S. A. McLuckey et al., "Selective Ion Isolation/Rejection Over a Broad Mass Range in the Quadrupole Ion Trap", *J. Am. Soc. Mass Spectrom*, 1991, vol. 2, pp. 11-21.

D. C. Muddiman et al., "Charge-State Reduction with Imrpoved Signal Intensity of Oligonucleotides in Electrospray Ionization Mass Spectrometry", *J. Am. Soc. Mass Spectrom*, 1996, vol. 7, pp. 697-706.

R. E. March, "An Introduction to Quadrupole ion Trap Mass Spectrometry", *Journal of Mass Spectrometry*, 1997, vol. 32, pp. 351-369.

A. H. Payne et al., "Gas-phase ion-ion interactions between peptides or proteins and iron ions in a quadrupole ion trap", *International Journal of Mass Spectrometry*, 2001, vol. 204, pp. 47-54.

R. R. O. Loo et al., "Protein Structural Effects in Gas Phase Ion/ Molecule Reactions with Diethylamine", *Rapid Communications in Mass Spectrometry*, 1992, vol. 6, pp. 159-165.

M. G. Ikonomou et al., "An ion source with which ions produced by electrospray can be subjected to ion/molecule reactions at intermediate pressures (10-100 Torr.) Deprotonation of polyprotonated peptides", *International Journal of Mass Spectrometry and Ion Processes*, 1992, vol. 117, pp. 283-298.

B. E. Winger et al., "Gas-Phase Proton Transfer Reactions Involving Multiply Charged Cytochrome c Ions and Water Under Thermal Conditions", *J. Am. Soc. Mass Spectrom*, 1992, vol. 3, pp. 624-630.

D. S. Gross, et al., "Experimental Measurement of Coulomb Energy and Intrinsic Dielectric Polarizability of a Mul[iply Protonated Peptide Ion Using Electrospray Ionization Fourier-Transform Mass Spectrometry", *J. Am. Chem. Soc.*, 1995, vol. 117, No. 3, pp. 883-890.

C. J. Cassady et al., "Elucidation of Isometric Structures for Ubiquitin $[M+12H]^{12}+$ Ions Produced by Electrospray Ionization Mass Spectrometry", *J. Mass Spectrom*, 1996, vol. 31, pp. 247-254.

J. D. Williams et al., "Resonance Ejection Ion Trap Mass Spectrometry and Nonlinear Field Contributions: The Effect of Scan Direction on Mass Resolution", *Anal. Chem.*, 1994, vol. 66, No. 5, pp. 725-729.

J. N. Louris et al., "Instrumentation, Applications, and Energy Deposition in Quadrupole Ion-Trop Tandem Mass Spectrometry", *Anal. Chem.*, 1987, vol. 59, No. 13, pp. 1677-1685.

Aebersold, Ruedi, Goodlett, David R.; "Mass Spectrometry in Proteomics", Chem. Rev., vol. 101, No. 2, 2001, pp. 269-295.

Badman, Ethan R., Chrisman, Paul A., McLuckey, Scott A., A Quadrupole Ion Trap Mass Spectrometer with Three Independent Ion Sources for the Study of Gas-Phase Ion/Ion Reactions, Anal. Chem. vol. 74, No. 24, Dec. 15, 2002, pp. 6237-6243.

Blackstock, Walter P., Weir, Malcolm P., "Proteomics: quantitative and physical mapping of cellular proteins", Reviews, Tibtech, vol. 17, Mar. 1999, pp. 121-127.

Budnik, Bogdan A., Zubarev, Roman A., "$MH^{2+}$ ion production from protonated polypeptides by electron impact: observation and determination of ionization energies and a cross-section", Chemical Physics Letters, vol. 316, Jan. 7, 2000, pp. 19-23.

Cargile, Benjamin J., McLuckey, Scott A., Stephenson, Jr., James L., "Identification of Bacteriophase MS2 Coat Protein from *E. coli* Lysates via Ion Trap Collisional Activation of Intact Protein Ions", Anal. Chem. vol. 73, No. 6, Mar. 15, 2001, pp. 1277-1285.

Dove, Alan, "Proteomics: translating genomics into products?", Nature Biotechnology, vol. 17, Mar. 1999, pp. 233-236.

Dongre, Ashok R., Jones, Jennifer L., Somogyi, Arpad, Wysocki, Vicki H., "Influence of Peptide Composition, Gas-Phase Basicity, and Chemical Modification on Fragmentation Efficiency: Evidence for the Mobile Proton Model", J. Am. Chem. Soc., vol. 118, No. 35, 1996, pp. 8365-8374.

Eng, Jimmy K., McCormack, Ashley L., Yates III, John R., An Approach to Correlate Tandem Mass Spectral Data of Peptides with Amino Acid Sequences in a Protein Database, J. Am. Mass Spectrom,, vol. 5, 1994, pp. 976-989.

Fenn, John B., Mann, Matthias, Meng, Chin Kai, Wong, Shek Fu, Electrospray ioniation—principles and practice, Mass Spectrometry Reviews, vol. 9, 1990, pp. 37-70.

Fenn, John B., Mann, Matthias, Meng, Chin Kai, Wong, Shek Fu, Whitehouse, Craig M., "Electrospray Ionization for Mass Spectrometry of Large Biomolecules", Science, vol. 246, Oct. 6, 1989, pp. 64-71.

He, Min, McLuckey, Scott A., "Two Ion/ion Charge Inversion Steps to Form a Doubly Protonated Peptide from a Singly Protonated Peptide in the Gas Phase", J. Am. Chem. Soc., vol. 125, No. 26, 2003, pp. 7756-7757.

He, Min, Reid, Gavin E., Shang, Hao, Lee, Gil U., McLuckey, Scott A., "Dissociation of Multiple Protein Ion Charge States Following a Single Gas-Phase Purification and Concentration Procedure", Analytical Chemistry, vol. 74, No. 18, Sep. 15, 2002, pp. 4653-4661.

Herron, William J., Goeringer, Douglas E., McLuckey, Scott A., "Product Ion Charge State Determination via Ion/Ion Proton Transfer Reactions", Analytical Chemistry, vol. 68, No. 2, Jan. 16, 1996, pp. 257-262.

Herron, William J., Goeringer, Douglas E., McLuckey, Scott A., "Gas-Phase Electron Transfer Reactions from Multiply-Charged Anions to Rare Gas Cations", J. Am. Chem. Soc., vol. 117, No. 46, 1995, pp. 11555-11562.

Hogan, Jason M., McLuckey, Scott A., "Charge state dependent collision-induced dissociation of native and reduced porcine elastase", J. Mass Spectrom., vol. 38, No. 3, Mar. 3, 2003, pp. 245-256.

Horn, David M. Zubarev, Roman A., McLafferty, Fred W., "Automated de novo sequencing of proteins by tandem high-resolution mass spectrometry", PNAS, vol. 97, No. 19, Sep. 12, 2000, pp. 10313-10317.

Karas, Michael, Hillenkamp, Franz, "Laser Desorption Ionization of Proteins with Molecular Masses Exceeding 10 000 Daltons", Anal. Chem., No. 60, No. 20, Oct. 15, 1988, pp. 2299-2301.

Karas, Michael, Gluckmann, Matthias, Schafer, Jurgen, "Ionization in matrix-assisted laser desorption/ionization: singly charged molecular ions are the lucky survivors", J. Mass Spectrom, vol. 35, 2000, pp. 1-12.

Kelleher, Neil L., Lin, Hong Y., Valaskovic, Gary A., Aaserud, David J., Fridriksson, Einar K., McLafferty, Fred W., "Top Down versus Bottom Up Protein Characterization by Tandem High-Resolution Mass Spectrometry", J. Am. Chem. Soc., vol. 121, No. 4, 1999, pp. 806-812.

Loo, Rachel R. Ogorzalek, Smith, Richard D., "Investigation of the Gas-Phase Structure of Electrosprayed Proteins Using Ion-Molecule Reactions", J. Am. Soc. Mass Spectrom., vol. 5, 1994, pp. 207-220.

Loo, Rachel R. Ogorzalek, Udseth, Harold R., Smith, Richard D., Evidence of Charge Inversion in the Reaction of Singly Charged Anions with Multiply Charge Macroions, J. Phys. Chem., vol. 95, No. 17, 1991, pp. 6412-6415.

McLuckey, Scott A., Van Berkel, Gary J., Glish, Gary L., "Reactions of Dimethylamine with Multiply Charged Ions of Cytochrome c", J. Am. Chem. Soc, vol. 112, No. 14, 1990, pp. 5668-5670.

McLuckey, Scott A., Glish, Gary L., Van Berkel, Gary J., "Charge Determination of Product Ions Formed from Collision-Induced Dissociation of Multiply Protonated Molecules via Ion/Molecule Reactions", Anal. Chem., vol. 63, No. 18, Sep. 15, 1991, pp. 1971-1978.

McLuckey, Scott A., Reid, Gavin E., Wells, J. Mitchell, "Ion Parking during Ion/Ion Reactions in Electrodynamic Ion Traps", Anal. Chem. vol. 74, No. 2, Jan. 15, 2002, pp. 336-346.

McLuckey, Scott A., Stephenson, Jr., James L., "Ion/Ion Chemistry of High-Mass Multiply Charged Ions", Mass Spectometry Reviews, vol. 17, 1998, pp. 369-407.

Mortz, Ejvind, O'Connor, Peter B., Roepstorff, Peter, Kelleher, Neil L., Wood, Troy D., McLafferty, Fred W., Mann, Matthias, "Sequence tag identification of intact proteins by matching tandem mass spectral data against sequence data bases", Proc. Natl. Acad. Sci. USA, vol. 93, Aug. 1996, pp. 8264-8267.

Nemeth-Crawley, Jennfer F., Rouse, Jason C., "Identification and sequencing analysis of intact proteins via collision-induced dissociation and quadrupole time-of-flight mass spectrometry", J. Mass Spectrom., vol. 37, 2002, pp. 270-282.

Nielson, Michael L., Budnik, Bogdan, Haselmann, Kim F., Zubarev, Roman A., "Tandem MALDI/EI ionization for tandem Fourier transform ion cyclotron resonance mass spectrometry of polypeptides", International Journal of Mass Spectrometry, vol. 226, 2003, pp. 181-187.

Pandey, Akhilesh, Mann, Matthias, "Proteomics to study genes and genomes", Nature, vol. 405, Jun. 15, 2000, pp. 837-846.

Reid, Gavin E., Shang, Hao, Hogan, Jason M., Lee, Gil U., McLuckey, Scott A., "Gas-Phase Concentration, Purification, and Identification of Whole Proteins from Complex Mixtures", J. Am. Chem. Soc. vol. 124, No. 25, 2002, pp. 7353-7362.

Reid, Gavin E., McLuckey, Scott A., "Top down protein characterization via tandem mass spectrometry", J. Mass Spectrom., vol. 37, 2002, pp. 663-675.

Reid, Gavin E., Wu, Jin, Chrisman, Paul A., Wells, J. Mitchell, McLuckey, Scott A., "Charge-State-Dependent Sequence Analysis of Protonated Ubiquitin Ions via Ion Trap Tandem Mass Spectrometry", Anal. Chem. vol. 73, No. 14, Jul. 15, 2001, pp. 3274-3281.

Schaaff, T. Gregory, Cargile, Benjamin J., Stephenson, Jr., James L., McLuckey, Scott A., "Ion Trap Collisional Activation of the $(M+2H)^{2+}$—$(M+17H)^{17+}$ Ions of Human Hemoglobin β-Chain", Anal. Chem., vol. 72, No. 5, Mar. 1, 2000, pp. 899-907.

Scalf, Mark, Westphall, Michael S., Smith, Lloyd M., "Charge Reduction Electrospray Mass Spectrometry", Anal. Chem., vol. 72, No. 1, Jan. 1, 2000, pp. 52-60.

Scalf, Mark, Westphall, Michael S., Krause, Joern, Kaufman, Stanley L., Smith, Lloyd M., "Controlling Charge States of Large Ions", Science, vol. 283, Jan. 8, 1999, pp. 194-197.

Stephenson, Jr., James L., McLuckey, Scott A., "Simplification of Product Ion Spectra Derived from Multiply Charged Parent Ions via Ion/Ion Chemistry", Anal. Chem., vol. 70, No. 17, Sep. 1, 1998, pp. 3533-3544.

Stephenson, Jr., James L., McLuckey, Scott A., "Ion/Ion Reactions for Oligopeptide Mixture Analysis: Application to Mixtures Comprised of 0.5-100 kDa Components", J. Am. Soc. Mass Spectrom., vol. 9, 1998, pp. 585-596.

Stephenson, Jr., James L., McLuckey, Scott A., "Charge Manipulation for Improved Mass Determination of High-mass Species and Mixture Components by Electrospray Mass Spectrometry", J. Mass Spectrom., vol. 33, 1998, pp. 664-672.

Stephenson, Jr., James L., McLuckey, Scott A., "Ion/Ion Proton Transfer Reactions for Protein Mixture Analysis", Anal. Chem., vol. 68, No. 22, Nov. 15, 1996, pp. 4026-4032.

Stephenson, Jr., James L., McLuckey, Scott A., "Ion/Ion Reactions in the Gas Phase: Proton Transfer Reactions Involving Multiply-Charged Proteins", J. Am. Chem. Soc. vol. 118, No. 31, 1996, pp. 7390-7397.

Wells, J. Mitchell, Chrisman, Paul A., McLuckey, Scott A., "'Dueling' ESI: Instrumentation to Study Ion/Ion Reactions of Electrospray-generated Cations and Anions", J. Am. Soc. Mass Spectrom., vol. 13, 2002, pp. 614-622.

Wells, J. Mitchell, Chrisman, Paul A., McLuckey, Scott A., "Formation of Protein—Protein Complexes in Vacuo", J. Am. Chem. Soc., vol. 123, No. 49, 2001, pp. 12428-12429.

Williams, Evan R., "Proton Transfer Reactivity of Large Multiply Charged Ions", J. Mass Spectrom., vol. 31, 1996, pp. 831-842.

Zubarev, Roman A., Horn, David M., Fridriksson, Einar K., Kelleher, Neil L., Kruger, Nathan A., Lewis, Mark A., Carpenter, Barry K., McLafferty, Fred W., "Electron Capture Dissociation for Structural Characterization of Multiply Charged Protein Cations", Anal. Chem., vol. 72, No. 3, Feb. 1, 2000, pp. 563-573.

Zubarev, Roman A., Kelleher, Neil L., McLafferty, Fred W., "Electron Capture Dissociation of Multiply Charged Proteins Cations. A Nonergodic Process", J. Am. Chem. Soc., vol. 120, No. 13, 1998, pp. 3265-3266.

Zubarev, Roman A., Kruger, Nathan A., Fridriksson, Einar K., Lewis, Mark A., Horn, David M., Carpenter, Barry K., McLafferty, Fred W., "Electron Capture Dissociation of Gaseous Multiply-Charged Proteins Is Favored at Disulfide Bonds and Other Sites of High Hydrogen Atom Affinity", J. Am. Chem. Soc., vol. 121, No. 12, 1999, pp. 2857-2862.

* cited by examiner

PROCESS FOR INCREASING IONIC CHARGE IN MASS SPECTROMETRY

GOVERNMENT RIGHTS

This invention was funded in part by the National Institutes of Health, under Grant No. GM 45372, and The United States Department of Energy, under Award No. DE-FG 02-00ER15105. The Government may have certain rights in this invention.

CROSS REFERENCE TO RELATED APPLICATIONS, AS FOLLOWS:

This patent application is a U.S. national counterpart application, filed under 35 U.S.C. § 371(c), of international application Ser. No. PCT/US2003/017022 filed May 30, 2003.

FIELD OF THE INVENTION

This invention relates to the analysis of molecules by mass spectrometry. In particular, this invention relates to the analysis of molecules that may possess multiple charges by mass spectrometry by increasing the charge on the molecules.

BACKGROUND OF THE INVENTION

The analysis of large molecules by mass spectrometry is playing an increasingly important role in modern biological research. Such analysis is facilitated by recent advances in the ability to generate gas-phase ions of these large molecules. Mass spectrometry is particularly suited to the analysis of these biological materials because they are often available only in small quantities, typically as isolates from natural sources. In addition, mass spectrometry is well suited to the area of proteomics, which includes the study of the time-dependent protein complement of an organism.

Large biologically derived molecules are often biopolymers such as proteins, peptides, nucleic acids, oligonucleotides, polysaccharides, and oligosaccharides. The identification and analysis of these biopolymers are dependent on a sufficient amount of fragments, and a sufficient diversity in the fragmentation patterns that may be generated during mass spectrometry. These fragments and fragmentation patterns are interpreted to derive the primary sequence of the biopolymers. Further, the number of and diversity of the fragments generated by mass spectrometry is often dependent upon the number of and diversity of the charges and charge states that may be generated on the molecule. Processes and apparatus for manipulating and modifying these charge states to optimize the observed fragmentation will expand the field of mass spectrometric analysis of biologically derived molecules.

SUMMARY OF THE INVENTION

Processes for analyzing molecules by mass spectrometry are described herein. These processes use the technique of generating an initial charge on the molecule to be analyzed, placing that molecule into a gaseous phase, and manipulating or modifying that initial charge.

The initial charge is generated using techniques that include but are not limited to plasma desorption ionization (PDI), field desorption ionization (FDI), electrohydrodynamic ionization (EHI), laser desorption ionization (LDI), matrix assisted laser desorption ionization (MALDI), atmospheric pressure matrix assisted laser desorption ionization (APMALDI), spray ionization techniques, including electrospray ionization (ESI), nano-electrospray ionization, thermospray ionization (TSI), aerospray ionization (ASI), sonic spray ionization (SSI), particle desorption methods such as fast atom bombardment (FAB), fast ion bombardment (FIB), such as secondary ion mass spectrometry (SIMS), and massive cluster impact, and the like.

After the initial charge is generated, an ion storage or trapping procedure is performed. Ions may be stored or trapped in any of a variety of devices including but not limited to linear ion traps, quadrupole ion traps, and the like. In some embodiments of the processes described herein, the initially generated ions are directed to the ion storage device by illustratively using a turning quadrupole, and the like.

In one illustrative embodiment, the initial charge is manipulated by contacting the initially charged molecule, or any charged fragments of that molecule, with at least one multiply charged ionic compound. The initial charge may be a single charge of either polarity or a multiple charge of either polarity. After contacting the initially charged molecule or charged fragment thereof with at least one multiply charged ionic compound, the initial charge on the molecule or fragment thereof is changed. Illustratively, the absolute value of the initial charge is lowered, or the polarity of the initial charge is changed. In the latter case where the polarity of the initial charge is changed, the absolute value of the resulting charge may therefore be greater than the absolute value of the initial charge.

In another illustrative embodiment, the initially charged molecule or charged fragment thereof is contacted with more than one multiply charged ionic compound. After contacting the initially charged molecule or charged fragment thereof with one multiply charged ionic compound, the initial charge on the molecule or fragment thereof is changed. Illustratively, the absolute value of the initial charge is lowered, or the polarity of the initial charge is changed. In the latter case where the polarity of the initial charge is changed, the absolute value of the resulting second charge may therefore be greater than the absolute value of the initial charge. Subsequently, the molecule or fragment thereof having the resulting second charge is contacted with a second multiply charged ionic compound. After contacting the molecule or fragment thereof having the second charge with the second multiply charged ionic compound, the resulting second charge on the molecule or fragment thereof is changed. Illustratively, the absolute value of the second charge is lowered, or the polarity of the second charge is changed. In the latter case where the polarity of the second charge is changed, the absolute value of the resulting third charge may therefore be greater than the absolute value of the second charge.

In one aspect, the polarity of initial charge is changed, and the resulting charge has an absolute value greater than the absolute value of the initial charge. In another aspect, the initial charge has an absolute value greater than one, and the resulting charge has an absolute value of one and the opposite polarity of the initial charge.

In another aspect, the polarity of the initial charge is changed after contacting a multiply charged ionic compound, and the polarity of the resulting second charge is changed back, or reverted, to the polarity of the first charge after contacting a second multiply charged ionic compound. In another aspect, the absolute value of the final charge is greater than the absolute value of the initial charge.

Prior to the manipulation or modification of the charge on the molecule or fragment thereof, or following the manipulation or modification of the charge on the molecule or fragment thereof, an optional mass filtering step is performed on one or more of the ions generated in the processes described herein. This mass selection step may be performed on the molecular ions, including fragment ions thereof prior to contact, or following contact with the multiply charged ionic compounds. This mass selection step may also be performed on any of the multiply charged ionic compounds that are contacted with the molecular ions or fragment ions thereof.

Prior to the manipulation or modification of the charge on the molecule or fragment thereof, or following the manipulation or modification of the charge on the molecule or fragment thereof, an optional mass analysis step is performed on one or more of the ions generated in the processes described herein. The mass analysis step may use any of a variety of techniques including but not limited to scanning from a linear ion trap, scanning from a quadrupole ion trap, time of flight (TOF), ion cyclotron resonance, and the like.

The processes described herein may also include a step of concentrating the charge of the molecule or fragment thereof using any of a variety of techniques including but not limited to atmospheric sampling glow discharge ionization (ASGDI), and the like.

Apparatus for performing the processes described herein are also described. Various configurations are constructed from those components necessary to perform the steps of the processes described herein, including (1) various sources for generating ions or charges on molecules or analytes to be analyzed, (2) various components for storing or trapping those molecular ions or fragment ions thereof so-generated, including components for directing ions to such storage components, (3) various components for optionally filtering or selecting certain masses from those molecular ions or fragment ions thereof, (4) various components for providing a reaction environment for contacting other charged or multiply charged ionic compounds with those molecular ions or fragment ions thereof to modify the charge states of the molecular ions or fragment ions, and (5) various components for analyzing the molecular ions or fragment ions thereof.

DETAILED DESCRIPTION OF THE INVENTION

The initial charge on a molecule or analyte to be ultimately analyzed by mass spectrometry may be generated by any of the variety of techniques including but not limited to those commonly employed in mass spectrometric analysis, such as plasma desorption ionization (PDI), field desorption ionization (FDI), electrohydrodynamic ionization (EHI), laser desorption ionization (LDI), matrix assisted laser desorption ionization (MALDI), atmospheric pressure matrix assisted laser desorption ionization (APMALDI), spray ionization techniques, including electrospray ionization (ESI), nano-electrospray ionization, thermospray ionization (TSI), aerospray ionization (ASI), sonic spray ionization (SSI), particle desorption methods such as fast atom bombardment (FAB), fast ion bombardment (FIB), such as secondary ion mass spectrometry (SIMS), and massive cluster impact, and the like. The initial ionizing source includes but is not limited to fast atoms such as xenon, argon, and the like, slow electrons, high energy electrons, and clusters such as glycerol clusters, and the like. It is appreciated that the processes described herein are not limited by the method used to generate the ions used in these processes, and further that the ionization method may use either charged or uncharged substances to generate the initial charge on the molecule or analyte.

It is appreciated that depending upon the nature of the analyte or molecule to be detected, either a positive charge or a negative charge may be generated during initial ionization, and therefore the selection of the ionization technique is conveniently chosen after considering the nature of the analyte or molecule. Further, in order for an analysis to take place, a variety of procedures may be followed to introduce a sample containing the analyte or molecule into the apparatus wherein the initial charge is generated. Those procedures include but are not limited to those common to the field of mass spectrometry, such as introduction of the sample as a solution, which is aspirated, volatilized, or atomized, or introduction of the sample as a solid or liquid, which may be adhered to a probe or other solid surface, such as a matrix.

It is also appreciated that certain molecules may form a positive charge more easily than a negative charge, while other molecules may form a negative charge more easily than a positive charge. For example, ambident molecules, such as peptides and proteins, may form with relative ease either a positive ion or a negative ion. However, certain carbohydrates may form positive ions more readily than negative ions. In contrast, certain oligonucleotides and nucleic acids may form negative charges more readily than positive ions.

Peptides and proteins are analyzed by the processes and apparatus described herein, and may be widely varying in both primary sequence and molecular weight. Peptides and proteins, that may be analyzed include but are not limited to bradykinin, ubiquitin, cytochrome C, hemoglobin, and the like. Oligosaccharides and carbohydrates are analyzed by the processes and apparatus described herein, and may be widely varying in both primary sequence and molecular weight. The oligonucleotides and nucleic acids that may be analyzed by the processes described herein are widely varying in both primary sequence and molecular weight. The oligonucleotides and nucleic acids that may be analyzed include but are not limited to oligonucleotides isolated from natural sources and synthetic oligonucleotides, having illustratively from about 5 to about 50 nucleotides. In addition, nucleic acids, including nucleic acids from plants, animals, bacteria, and the like, including very large nucleic acids that have more than about 100 kilobases may be analyzed using the processes and apparatus described herein.

It is understood that any molecule that may be ionized into a gaseous state using any of the techniques described herein or any other technique known to produce ionized molecules in the gas phase, may be analyzed by the processes described herein provided that charge states of both polarities may be formed on the molecule, and that at least one of those charge states has an absolute value greater than one. Though the generation of multiple charges on a molecule or analyte prior to analysis is more often desired in molecules and analytes having high molecular weights, the processes and apparatus described herein are equally applicable to the analysis of smaller molecules, where it is desirable to generate higher charge states or multiple charges thereon. Without being bound by theory, the generation of multiple charges on a molecule may account for an increase in the number of fragments generated, and to the degree of, and the diversity of the fragmentation observed. It is appreciated that increased fragmentation and increased fragmentation diversity may enhance the ability to identify the chemical composition or chemical structure, including the primary sequence of large molecules, such as various biological compounds including proteins, nucleic acids, and polysaccharides.

Depending upon the technique used to generate the initial charge, and depending upon the nature of the molecule to be detected, the initial charge may therefore be positive or negative. In addition, the initial charge on the molecule may have an absolute value of one or alternatively, the initial charge on the molecule may have an absolute value greater than one. In the case where the initial charge is greater than one, the initial charge may be optionally concentrated to a lower selected charge by using a suitably configured concentrating component that uses the technique of ion parking. Ion parking is generally described in U.S. Pat. No. 4,849,628 to McLuckey et al., the disclosure of which is incorporated herein by reference. It is appreciate that the technique of ion parking is advantageously used in processes where the molecular ions or fragment ions form a population of charge states of simultaneously varying values. Such a condition may complicate the interpretation of the resulting mass spectrum. Concentrating the various charge states to a single state will generally simplify the mass spectrum obtained.

Alternatively, using a conveniently placed component such as an atmospheric sampling glow discharge ionization (ASGDI) source, and the like, the absolute value of the initial charge may be reduced one charge at a time, in a stepwise fashion. An ASGDI is capable if reducing the absolute value of both positively charged and negatively charged molecular ions or fragments thereof In one aspect the ASGDI source uses monoanions of perfluorocarbons, such as perfluoro-1,3-dimethylcyclohexane (PDCH). In the case where the initial charge is both greater than one and positive, the initial charge may be optionally lowered to a lower selected charge, including a charge of negative one, by using a suitably configured electron capture dissociation (ECD) component.

In either the case of an initial ionization having an absolute value of one or greater than one, the charge of the molecular ion so generated, may be changed to a charge having an absolute value equal to or greater than one, but of opposite polarity to the charge generated initially. Such a conversion is accomplished by contacting the molecular ion, illustratively in the gas phase, with a multiply charged ionic compound. A great variety of multiply charged ionic compounds may be used for this purpose of polarity change in the processes described herein.

The multiply charged ionic compounds useful in the processes described herein include but are not limited to polyionic compounds having multiple functional groups that may each form a net charge or a plurality of charges under conditions that may be created in typical mass spectrometric analyses and apparatus. Such molecules include but are not limited to compounds having a plurality of amine groups, heteroaromatic amine groups, imine groups, hydrazine groups, guanidine groups, carboxylic acid groups, sulfonic acid groups, phosphonic acid groups, and the like. The multiply charged ionic compounds described herein include polymeric materials, such as dendrimers, and naturally occurring polymeric materials such as nucleic acids and proteins. Illustratively, $(5'\text{-}d(AAAA)\text{-}3')^{3-}$, $(melittin+4H)^{4+}$, $(horse\ myoglobin+20H)^{20+}$, $(holomyoglobin+9H)^{9+}$, and cytochrome C and apomyoglobin carrying multiple charges are useful in the processes described herein.

It is appreciated that such compounds may possess a mixture of like-charged groups, such as compounds that possess both carboxylic acid groups and sulfonic acid groups, or compounds that possess both ammonium and iminium groups. Further, it is appreciated that a mixture of compounds may be used in the processes described herein for changing the charge on the analyte or molecule to be detected, such as a mixture of a polyamine compound and a polyimine compound.

Multiply charged ionic compounds having a plurality of negatively charged groups include aromatic groups having a plurality of carboxylic acid groups present thereon, including alkylcarboxylates, cycloalkylcarboxylates, arylcarboxylates, such as phenyl-dicarboxylic, -tricarboxylic, and tetracarboxylic acids, arylalkylcarboxylates, such as phenyl-dipropionic, tripropionic, and tetrapropionic acids, and phenyl-diacetic, triacetic, and tetraacetic acids, and the like. In addition, dendrimers having multiple carboxylic acid, sulfonic acid, or phosphonic acid functionalities are useful in the processes described herein.

Multiply charged ionic compounds having a plurality of positively charged groups include aminoalkyl, hydrazinoalkyl, guanidinoalkyl, aminocycloalkyl, hydrazinocycloalkyl, guanidinocycloalkyl, aminoaryl, hydrazinoaryl, guanidinoaryl, heteroaromatic amines, such as pyridinyls, pyrimidinyls, pyridazinyls, pyrazinyls, imidazolinyls, oxazolihnyls, pyrrolyls, pyrazolyls, indolyls, quinolinyls, quinazolinyls groups, and the like. Illustratively, dendrimers having multiple ammonium or iminium groups, including alkyleneammonium and alkyleneiminium functionalities are useful in the processes described herein. Dendrimers useful in the processes described herein include but are not limited to cyclotriphosphazene-phenoxymethyl(methylhydrazono) (PMMH) dendrimers, Polypropylenimine hexadecaamine Dendrimers, Polypropylenimine dotriacontaamine Dendrimers, Polypropylenimine tetraamine Dendrimers, Polypropylenimine tetrahexacontaamine Dendrimers, any of the various polyamidoamine (PAMAM) dendrimers, and any of the various primary-amine terminated dendrimers.

It is understood that many dendrimers are commercially available as a mixture of dendrimers with a single compound having a specified number of chargeable functional groups present thereon. In these cases, it is appreciated that following the preparation of the multiply charged ionic compound from the dendrimer, a mass selection procedure may be advantageously included as a step in the processes described herein. Such a mass selection procedure will have the benefit of decreasing the noise observed in the final mass spectrum and simplifying the interpretation of the resulting mass spectrum. The mass selection process may be accomplished using any of a variety of techniques common to mass spectrometry, including quadrupole ion traps, linear ion traps, time of flight (TOF), and ion cyclotron resonance. In such a step, the lower and higher molecular weight compounds, as well as the compounds that do not have the desired number of chargeable groups present in the multiply charged ionic compound precursor are removed. The resulting purified multiply charged ionic compound may then be contacted with the molecule or analyte. Similarly, in certain aspects of the processes described herein, a mass selection or mass filtering step may be included where the initially generated molecular ions or fragment ions thereof are separated. In these embodiments, only certain charged ionization states, or certain mass ranges are contacted with the multiply charged ionic compounds. A process that uses the principle of tandem mass spectrometry may include such a filtering or selection procedure.

It is also appreciated that during the course of a polarity change on the molecule or fragment thereof, in some embodiments of the invention, aggregates of these ions and the multiply charged ionic compound may form. These aggregates also have the overall effect of changing the charge on the molecule, including changing the charge on the molecule to a value opposite in polarity. However, in these cases the charge is changed by the aggregation of the multiply charged ionic compound with the analyte ion rather than the transfer of either an electron or a proton between the multiply charged ionic compound and the analyte or molecular ion. In either case, the detection of the analyte by mass spectrometry is accomplished by evaluating the masses that are produced in the apparatus. Mustratively, a protein having an initial charge of for example of positive one, may form an aggregate in the ion trap with a multiply charged ionic compound that is for example an aryl(tetraalkylenecarboxylate), where the aggregate has an overall charge of negative three.

In configurations of the processes described herein where there is included a tandem mass spectrometry procedure, also known as MS/MS, it is understood that such aggregates may yet be analyzed by these techniques commonly in use, following a heat treating step, where the aggregate molecule comprising the analyte or molecular ion and the multiply charged ionic compound are separated in a fashion where the analyte of molecular ion retains the increased charge state.

The polarity change of the initial charge on the analyte or molecule or fragment thereof may result in a second charge state that has an absolute value greater than or equal to the absolute value of the initial charge state. In other aspects, the polarity change of the initial charge on the analyte or molecule or fragment thereof may result in a second charge state that has an absolute value less than or equal to the absolute value of the initial charge state. Further, the third charge may have an absolute value greater than or equal to the absolute value of the second charge state. Illustratively, the third charge state has an absolute value greater than the absolute value of the initial charge on the analyte or molecule or fragment thereof.

It is understood that the molecule or analyte may undergo fragmentation at various times during the operation of the processes described herein to produce fragment ions, and at various times during the modification of the charges thereon. The foregoing discussion regarding the subsequent processes and process steps apply equally to these fragment ions as to the molecular ions or analyte ions described above. For example, a protein-based analyte may illustratively fragment upon initial ionization to a plurality of charged ion fragments, each having a first charge that may be the same or different. The unfragmented molecular ion may also be included in this group. Each molecular ion or fragment ion thereof is then contacted with a multiply charged ionic compound, or a mixture of such compounds that change the charge state to a second charged state, the polarity of which is the opposite of the initial charge state. Optionally, this group of now-oppositely charged molecular or molecular fragment ions may be contacted with a second multiply charged ionic compound, or a second mixture of such compounds capable of changing the charge state to a third charge, where the third charge on any given molecular or molecular fragment ion is the same or different, but where each is the opposite polarity of the second charge. Additional fragmentation of the molecular ion or other fragmentation ions produced in the initial ionization may occur following either or both steps wherein the molecular ions or fragment ions are contacted with the one of more multiply charged ionic compounds. In the case of multiply charged molecular ions or fragment ions, further or differential fragmentation is optionally accomplished by including an electron capture dissociation (ECD) procedure, a collision-induced dissociation procedure, and the like.

As described herein, a mass filtering or mass selection procedure may also be introduced in the process following the modification of the initial or even the second charge state on the molecule or fragment thereof. This mass filtering or mass selection procedure is optionally accomplished using a scanning technique, such as by scanning the masses from a linear or quadrupole ion trap, and the like.

It is appreciated that the change between the first and second charge states, and the change between the second and third charge states may occur as a stepwise procedure, wherein a dwell time is introduced into the process to allow a substantial number of molecules or molecular fragments thereof to change charge states. Subsequently, the change between the second and third charge states is performed.

Alternatively, the change among charge states may occur in a contemporaneous manner, wherein a mixture of multiply charged ionic reagents or compounds comprises both positively charged ionic compounds and negatively charged ionic compounds. In this variation of the process, the molecular ion or molecular fragment ion undergoes two changes in polarity, each oppositely directed, in a one-step process. It is appreciated that the selection of positive and negative multiply charged ionic compounds is accomplished in a way to enhance the population of molecular ions or fragment ions that have a desired charge state. This enhancement may be derived through an understanding of the thermodynamics controlling the overall modification of the charge state on the molecular ion or fragment ion thereof. In one aspect, desirable thermodynamics favor the formation of a charge state on the molecular ion or molecular fragment ion that is the same as the initial charge state thereon, passing through a second charge state that is the opposite of the initial charge state, and having a final charge with an absolute value that is greater than the absolute value of the initial charge state. In one illustrative aspect, the second charge state has an absolute value of one. In another illustrative embodiment, both the initial charge state and the second charge state have an absolute value of one, and the third charge state has an absolute value greater than one.

The molecular ions generated in the processes described herein may also be analyzed, where such analysis includes detection of molecular ions or fragments thereof, and measurement of the masses of these molecular ions or fragments thereof that are produced in the processes or by the apparatus described herein. Such detection and measurement may be performed by using any of the variety of techniques commonly employed in mass spectrometric analysis, including but not limited to scanning from quadrupole ion traps, linear ion traps, analysis via time of flight (TOF), ion cyclotron resonance, and the like. Further, the detection and analysis may also include a tandem mass spectrometry configuration.

Figure 1:
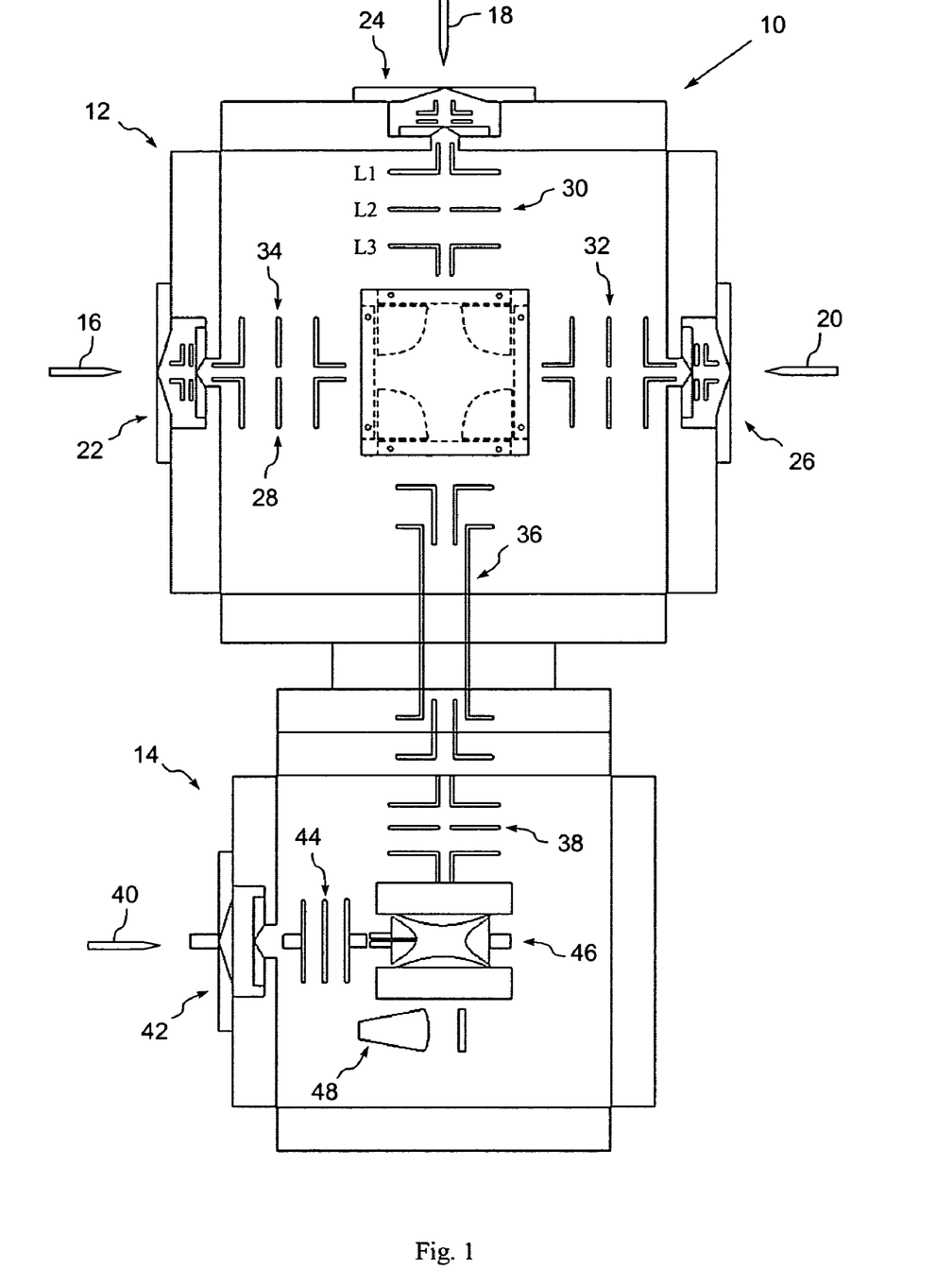
FIG. 1 illustrates an apparatus 10 for performing processes described herein.

The processes described herein may be performed by any variety of mass spectrometry equipment that is common to mass spectrometric analysis and has been configured with devices or components that are capable of performing the procedures required by the processes described herein. In general, the apparatus described herein are constructed from components or devices that are capable of performing functions required by the processes described herein, such as (1) various sources for generating ions or charges on molecules or analytes to be analyzed, (2) various components for storing or trapping those molecular ions or fragment ions thereof so-generated, including components for directing ions to such storage components, (3) various components for optionally filtering or selecting certain masses from those molecular ions or fragment ions thereof, (4) various components for providing a reaction environment for contacting other charged or multiply charged ionic compounds with those molecular ions or fragment ions thereof to modify the charge states of the molecular ions or fragment ions, and (5) various components for analyzing the molecular ions or fragment ions thereof. It is appreciated that the apparatus described herein may also be capable of performing other processes in addition to those described herein. Such flexibility possessed by an apparatus should not be understood to suggest that apparatus is excluded from the invention described herein FIG. 1 illustrates one such configuration 10. This configuration is intended to illustrate one of many possible configurations of apparatus capable of performing the processes described herein. The configuration comprises a first housing component 12 and a second housing component 14. The first housing component 12 possesses a first generating source 16, a second generating source 18, and a third generating source 20. The generating sources 16, 18, and 20 each interface with the first housing component 12 through first, second, and third interface regions 22, 24, and 26, respectively, such as a first, second, and third atmosphere vacuum interface. The interface regions 22, 24, and 26 are each coupled to a first, second, and third general ion optical element 28, 30, and 32, respectively, such as a first, second, and third electrostatic lens assembly, each comprising lenses L1, L2, and L3. Each general ion optical element 28, 30, and 32 is aimed into a turning quadrupole 34 which is capable of diverting the ions generated from the generating sources 16, 18, and 20 into an ion transmission device 36, such as a tube lens or a quadrupole mass selector. The ion transmission device 36 couples the first housing component 12 to the second housing component 14. In addition, the ion transmission device 36 is coupled to a fifth general ion optical element 38, which is aimed into a quadrupole ion trap 46.

The second housing component 14 possesses a fourth generating source 40, such as an atmospheric sampling glow discharge ionization source, interfaced with the second housing component 14 through a fourth interface region 42. The fourth interface region 42 is coupled to a fourth general ion optical element 44 which is aimed into the quadrupole ion trap 46. The charges on ions that have been generated in the first housing component 12 and diverted into the ion trap 46 in the second housing component may be changed by the introduction of multiply charged ionic compounds as described herein, and generated illustratively in the first housing component 12, or by ions generated from the fourth ion source 40. The second housing component 14 also possesses a detector 48, such as an electron multiplier, for detecting ions released or ejected from the ion trap 46.

In FIG. 1, the apparatus is configured such that multiple sources are present for the optional generation of the various positively and negatively charged molecules, analytes, or multiply charged ionic compounds described herein. It is appreciated that all of these sources may not be required in some variations of the process. Further, the sources may be of the same character, such as a plurality of ESI sources, or of a different character, such as an ESI, a LSI, and a SIMS source. Any combination of sources occupying the various bays may be included in the apparatus described herein. Illustratively, in one embodiment, the three sources may be an ESI source, a LDI source, and a FAB(+) source; while in another illustrative embodiment, the three sources may be a negative ESI source, a positive ESI source, and an APMALDI source.

In addition, FIG. 1 illustrates an apparatus where there are two components, the first comprising the generating sources and a tuning quadrupole, and the second component comprising the storage and contacting area and detecting features. It is appreciated that in other embodiments, all of these functional pieces may be configured in the same component, while in other illustrative embodiments, an additional component may house, for example, the detecting feature separate from the contacting area.

Illustratively, one source is used to generate an initial charge on the molecular ion. As described herein, the generation of the molecular ion may be accomplished using any of a variety of components that are capable of generating ions using plasma desorption ionization (PDI), field desorption ionization (FDI), electrohydrodynamic ionization (EHI), laser desorption ionization (LDI), matrix assisted laser desorption ionization (MALDI), atmospheric pressure matrix assisted laser desorption ionization (APMALDI), spray ionization techniques, including electrospray ionization (ESI), nano-electrospray ionization, thermospray ionization (TSI), aerospray ionization (ASI), sonic spray ionization (SSI), particle desorption methods such as fast atom bombardment (FAB), fast ion bombardment (FIB), such as secondary ion mass spectrometry (SIMS), and massive cluster impact, and the like.

In one embodiment, the source is a SSI source capable of generating both positively and negatively charged multiply charged ionic compounds. In that embodiment, the molecular ion or fragment ion may be sequentially contacted with each of these ionic compounds generated from the same source. In one illustrative configuration, the SSI source is combined with a linear ion trap. This configuration of the apparatus described herein is well-suited for a flow through process, where the source generates the initial charge on the molecule, and the resulting ions or fragment ions thereof are placed in the storage trap. Subsequently, the SSI source is used to generate a multiply charged ionic compound or compounds having one polarity. These ions are allowed to flow through the linear ion trap, which unlike a quadrupole ion trap is capable of holding only one polarity of charge at a time. After some predetermined time, the SSI source is used to generate a multiply charged ionic compound or compounds having the other polarity. This ion stream is then contacted with the molecular ions or fragment ions in the linear trap.

The apparatus described herein is illustratively configured to include a turning quadrupole capable of directing the ions so produced into a storage device or trap, such as a quadrupole ion trap or a linear ion trap. In order that multiple sources may be conveniently placed on the apparatus, a turning quadrupole may advantageously be used to direct the ions of interest into other components of the apparatus, such as the contacting or reaction vessel component. The various ions generated from the various corresponding sources are directed into the turning quadrupole by an electrostatic lens, a series of electrostatic lenses, an electrostatic lens assembly, such as an Einzellens, or other suitably configured general ion optical element. Initially, the molecular ion or fragment thereof is turned into the contacting component or storage trap.

In an alternate embodiment, the generating component may be configured to include a mass selecting component or mass filtering component, such as a quadrupole ion mass filter, linear ion mass filter, and the like. The mass selecting component will have the effect of purifying the ions, such as the molecular ions or the fragment ions, that are introduced into the contacting component via the turning quadrupole. This purification procedure may be applied to the initially generated molecular ions, or to any of the multiply charged ionic compounds used to modify the charges on the molecular ions or fragment ions thereof during the contacting procedure. Each source may be optionally configured with such a mass selecting component.

Apparatus described herein also include a contacting or reaction vessel component. In some embodiments, the contacting or reaction vessel component is a quadrupole ion trap or a linear ion trap. The contacting or reaction vessel component allows for the molecular ions or fragment ions initially generated, and optionally filtered to be contacted with multiply charged ionic compounds that will change the charges on the molecular ions or fragment ions. It is appreciated, that like the molecular ions or fragment ions that are initially generated, the charges generated on the multiply charged ionic compounds may also be mass filtered or mass selected prior to introduction into the reaction vessel component.

The contacting component includes a trap for the purpose of holding for a predetermined period of time the molecular ions or fragments ions thereof in contact with any one of the multiply charged ionic compounds. In addition, the trap portion of the contacting component has the purpose of holding the molecular ions or fragments ions thereof for subsequent ion concentration or ion parking procedures. In some configurations of the apparatus described herein, the ion storage device or ion trap is a linear ion trap or a quadrupole ion trap. A linear ion trap is a two-dimensional trap that may only store one charge state polarity at a time. A quadrupole ion trap is a three-dimensional trap that may store two charge state polarities at a time.

In apparatus where the generating component and the contacting component are separate, the generating component and the contacting component may be in fluid communication by a suitably placed ion transmission system, such as an electrostatic filter assembly, tube lens, an RF ion guide, and the like, or an electrodynamic ion transmission system such as an hexapole or an octapole, and the like. Alternatively, the tube lens may be configured to include a single mass selecting component that can be used as a mass filter of any substance generated by the various ionizing sources and directed into the ion trap. In this embodiment, the necessity of having a mass selecting component at each source may be thus alleviated.

Further, the contacting component or reaction chamber may also include a mass selecting or mass filtering component, a mass scanning component, and a mass detecting component, such as an electron multiplier. It is to be understood that while the apparatus illustrated in FIG. 1 uses a contacting component that includes a trap, a mass selecting or mass filtering component, and a mass scanning component embodied in a quadrupole ion trap, these components may be configured as separate components in alternative embodiments of the apparatus described herein.

Illustratively, the mass scanning component may be a TOF component rather than a quadrupole mass filter. In that configuration, a quadrupole ion trap is used to store and contact the molecular ions, and the TOF component is used to analyze the masses resulting from the charge modification. In addition, the mass storage and contacting component may be a linear ion trap, where the multiply charged ionic compounds are contacted with the molecular ion or fragment ion in a flow-type process rather than the batch-type process illustrated by the quadrupole ion storage embodiment. In this configuration, a SSI source is conveniently selected as it has the ability to generate both positive and negative ions, and is particularly suited for this type of flow-through embodiment. However, it is appreciated that various configurations of these components may be constructed to perform the processes described herein.

In some configurations of the apparatus described herein, analyte ions or fragment ions thereof, or molecular ions or fragment ions thereof are detected. Detection is accomplished by any of the variety of techniques common to the field of mass spectrometry, and includes electron multipliers, and the like. Prior to the detection, a mass selection or mass filtering procedure is optionally performed on the analyte ions or fragment ions thereof or molecular ions or fragment ions thereof. Such a mass filtering or mass selection procedure may be accomplished by scanning the masses with a quadrupole. In other embodiments, the mass filtering or mass selection procedure may be accomplished using a time of flight component that in one step permits separation of the masses.

In embodiments having a quadrupole ion trap serving as the contacting component, the ions to be analyzed and detected are released using any of a variety of common techniques, such as resonance ejection and the like, into the detecting component. In one aspect the detecting component is an electron multiplier and the like. In other aspects, the detecting component includes a conversion dynode.

The foregoing discussion sets forth many possible embodiments with various aspects of the invention described herein for both the processes and apparatus. However, it is appreciated that other embodiments arising from combinations of the components described herein or the procedures described herein though not explicitly set forth are nevertheless contemplated to fall within the scope of the invention as described herein. Further, the following illustrative examples are presented to provide an additional understanding of the nature and the spirit of the invention. The examples are intended to be illustrative and should not be considered to limit the invention in any way.

EXAMPLE 1

Figure 2A:
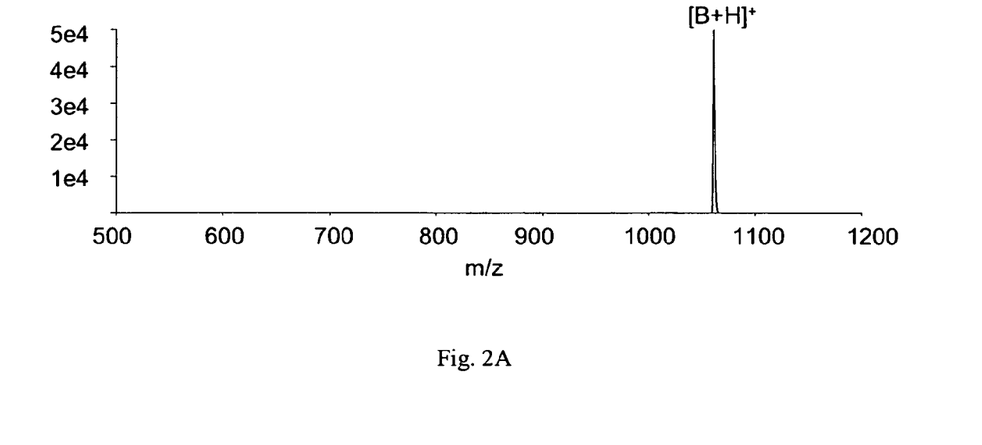
FIG. 2A illustrates an ESI mass spectrum of bradykinin showing the [B+H]$^+$ ion. The vertical axis is relative abundance in arbitrary units.
Figure 2B:
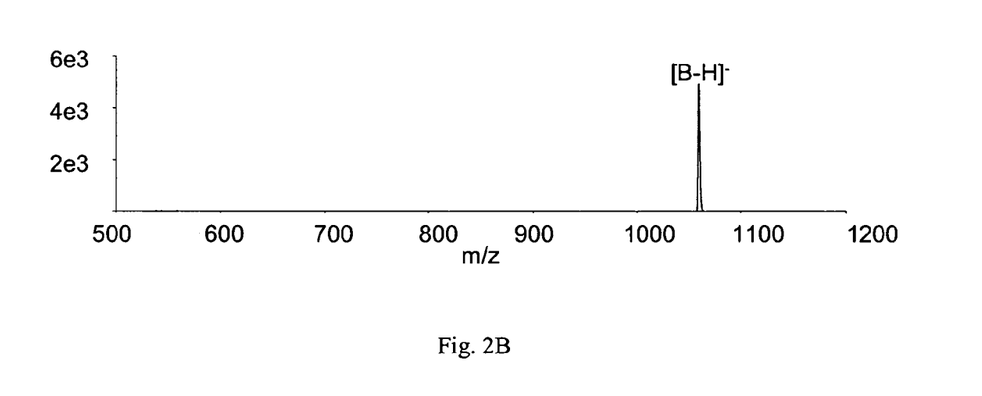
FIG. 2B illustrates a mass spectrum of bradykinin following treatment of the monocation of bradyknin with a dianion of benzene-1,4-bispropionic acid (PDPA) showing the [B–H]$^-$ ion. The vertical axis is relative abundance in arbitrary units.
Figure 2C:
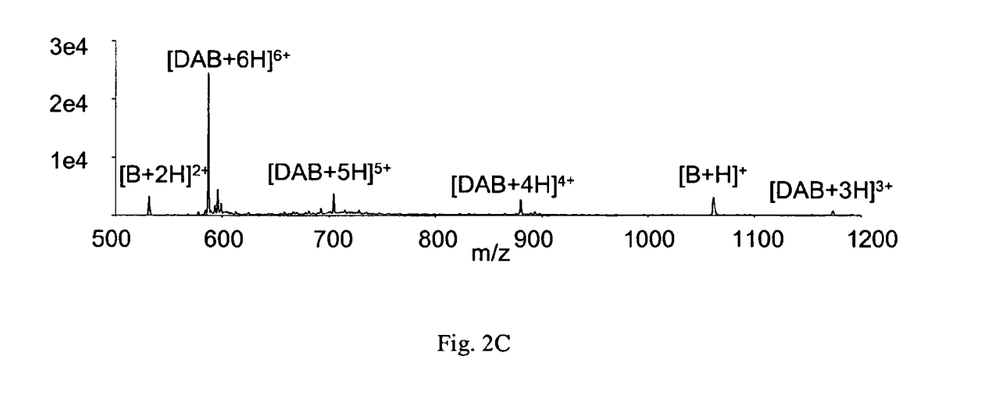
FIG. 2C illustrates a mass spectrum of bradykinin following treatment of the monoanion of bradykinin with a hexacation of poly(propyleneimine)dendrimer showing the [B+H]$^+$ ion and the [B+2H]$^{2+}$ ion. The vertical axis is relative abundance in arbitrary units.
Figure 3A:
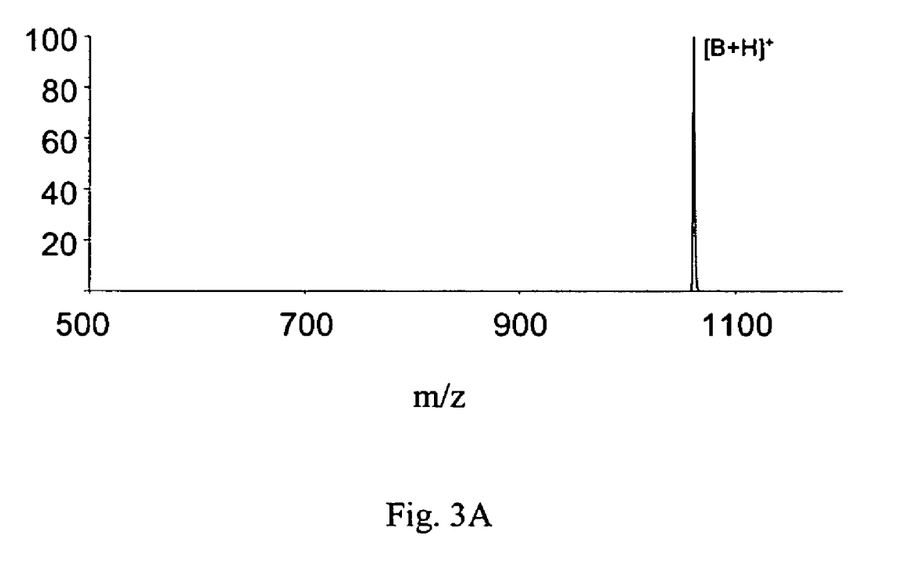
FIG. 3A illustrates an ESI mass spectrum of bradykinin showing the [B+H]$^+$ ion. The vertical axis is relative abundance in arbitrary units.
Figure 3B:
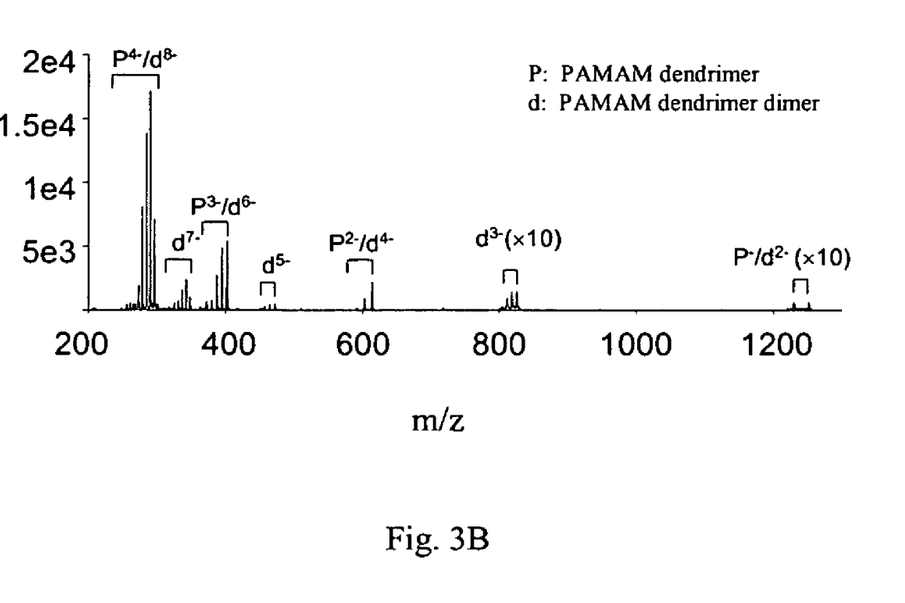
FIG. 3B illustrates an ESI mass spectrum of carboxylate terminated polyamidoamine dendrimer (generation 0.5) (PAMAM) showing multiple charge states on the dendrimer. The vertical axis is relative abundance in arbitrary units.
Figure 3C:
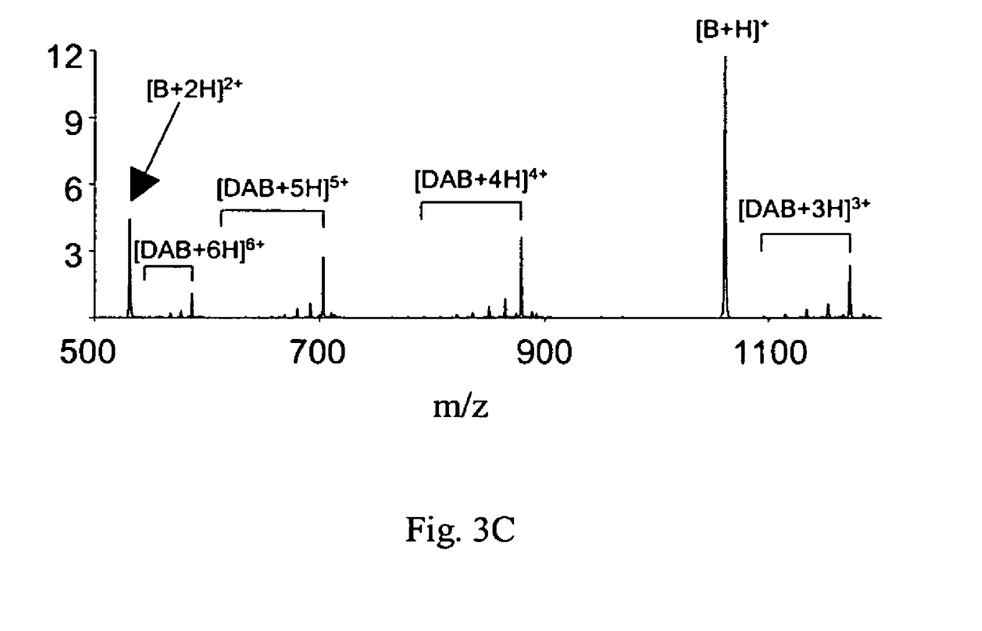
FIG. 3C illustrates a mass spectrum of bradykinin following treatment of the monoanion of bradykinin with a hexacation of poly(propylenimine) (1,4-diaminobutane (DAB) core, generation 4) dendrimer showing the [B+H]$^+$ ion and the [B+2H]$^{2+}$ ion. The vertical axis is relative abundance in arbitrary units.
Figure 3D:
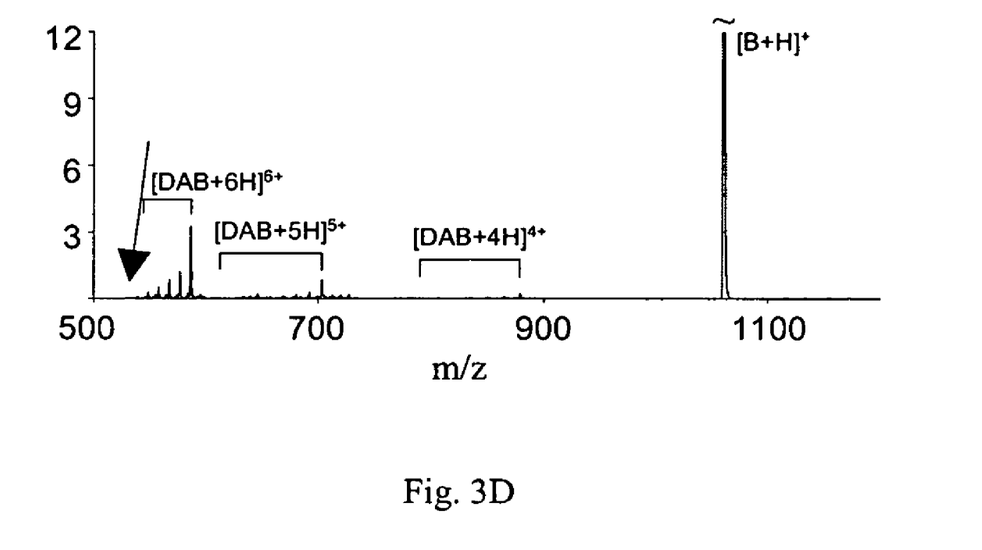
FIG. 3D illustrates a mass spectrum of bradykinin following treatment of the monocation of bradykinin with a hexacation of poly(propylenimine) (1,4-diaminobutane (DAB) core, generation 4) dendrimer showing only the [B+H]$^+$ ion and none of the [B+2H]$^{2+}$ ion. The vertical axis is relative abundance in arbitrary units.

Mass Spectrometric Analysis of Bradykinin with PDPA and Poly(propyleneimine) Dendrimer FIG. 2 summarizes results for an experiment in which bradykinin was subjected to two steps of charge inversion. FIG. 2A illustrates the positive ion electrospray mass spectrum of bradykinin after singly predominated ions of the protein were isolated in a quadrupole ion trap. FIG. 2B shows the spectrum that resulted after the bradykinin $(M+H)^+$ ion was contacted with multiply charged ionic compound paradibenzopropanoic acid (PDPA−2H)$^{2-}$. The formation of singly deprotonated bradykinin (M−H)$^-$ is observed in the spectrum shown in FIG. 2B. FIG. 2C shows the positive ion spectrum that resulted from the reaction of the multiply charged ionic compound (poly(propyleneimine) dendrimer+ 6H)$^{6+}$. The bradykinin (B+H)$^+$ ion reappears in addition to the bradykinin (B+2H)$^{2+}$ cation. A mass selection step was not performed on the multiply charged dendrimer. Therefore, the presence of various charge states of that dendrimer are seen as low level signals in the resulting mass spectrum shown in FIG. 2C.

EXAMPLE 2

Figure 4:
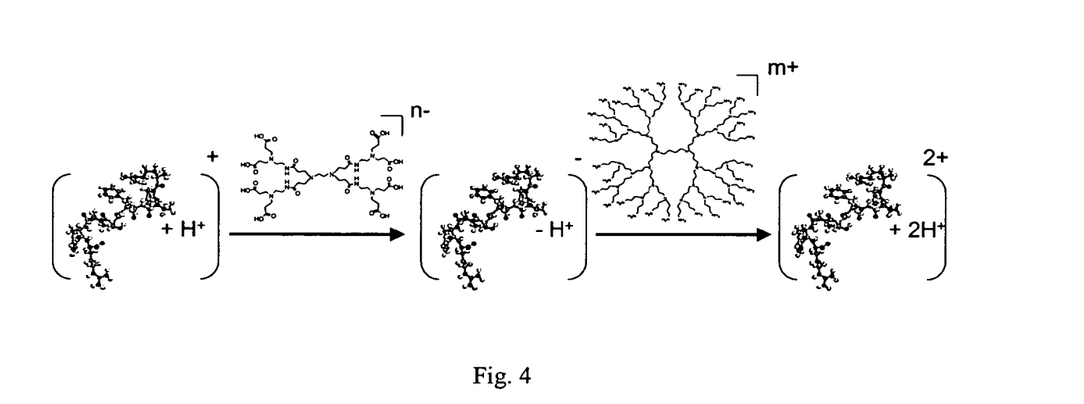
FIG. 4 illustrates the overall conversion of bradykinin to the (B+2H)$^{2+}$ ion.

Mass Spectrometric Analysis of Bradykinin with DAB Dendrimer and PAMAM Dendrimer FIG. 3 summarizes results for an experiment in which two steps of charge inversion were used to form the (B+2H)$^{2+}$ ions from the (B+H)$^+$ ions of bradykinin. The overall conversion of bradykinin to the (B+2H)$^{2+}$ ion is illustrated in FIG. 4. Solutions for nano-electrospray were prepared at concentrations of 1 mg/mL bradykinin and 5 mg/mL DAB dendrimers in aqueous 1% and 5% acetic acid (positive ions) or 1 mg/mL PAMAM dendrimer in 2% NH$_4$HCO$_3$ (negative ions). A full description of the ion trap mass spectrometer equipped with three ESI sources and ion optics that allow sequential injection of opposite polarity ions has been described in Badman et al., *Anal. Chem.*, 74, 6237-43 (2002), the disclosure of which is incorporated herein by reference. The first step of the experiment involved the accumulation of bradykinin ions formed via positive electrospray ionization in a quadrupole ion trap followed by isolation of the bradykinin (B+H)$^+$ ion. The resulting mass spectrum is shown in FIG. 3A. A population of anions formed via negative electrospray ionization of a carboxylate terminated polyamidoamine dendrimer (generation 0.5) (PAMAM) was then admitted into the ion trap and allowed to react with the bradykinin (B+H)$^+$ ions. The electrospray mass spectrum of the PAMAM reagent anions (no cations present) is shown in FIG. 3B. After reaction with the bradykinin (B+H)$^+$ ions, both residual PAMAM anions and (B−H)$^-$ bradykinin anions were observed in the spectrum (data not shown). The bradykinin (B−H)$^-$ ions were then isolated and a population of poly(propylenimine) (1,4-diaminobutane (DAB) core, generation 4)dendrimer cations formed via positive ion electrospray was admitted into the ion trap and allowed to react with the anions. The resulting product ion spectrum is shown in FIG. 3C. For comparison, the spectrum resulting from the sequence used to acquire the spectrum of FIG. 3C but without the admission of anions is shown in FIG. 3D. The latter spectrum shows the mixture of bradykinin (B+H)$^+$ and DAB dendrimer cations that resulted from the sequential injection of positive ions without the intervening anion accumulation and ion/ion reaction period. The position of the (B+2H)$^{2+}$ bradykinin ion on the mass-to-charge scale, if it were present, is indicated by an arrow. Several major differences can be noted in the comparison of FIGS. 3C and 3D. First, the charge state distribution of the DAB dendrimer ions has shifted to lower charge states as a result of partial neutralization with the bradykinin anions. Second, the abundance of the (B+H)$^+$ ion is significantly reduced (by roughly a factor of ten) by the admission of the anions. This is presumably due to losses associated with neutralization of part of the (B+H)$^+$ ion population by the PAMAM anions used to form (B−H)$^-$ ions, losses associated with neutralization of the (B−H)$^-$ anions in reactions with DAB cations, and losses associated with the fraction of ions formed as (B+2H)$^{2+}$ ions. Third, there is a clear signal that arises from the formation of the bradykinin (B+2H)$^{2+}$ ion. A roughly 200-fold increase over the background signal at the m/z ratio of the (B+2H)$^{2+}$ ion in FIG. 3D is observed in FIG. 3C. Net yields for bradykinin in the net reaction of (B+H)$^+$ →(B+H)$^-$→(B+2H)$^{2+}$ have been observed as high a 20% depending upon the reaction time permitted.

The invention claimed is:

1. A process for analyzing a molecule by mass spectrometry, comprising:
   (a) generating a first charge on the molecule;
   (b) changing the first charge on the molecule to a second charge; and
   (c) changing the second charge on the molecule to a third charge;
   where the second charge has the opposite polarity of the first charge, or the third charge has the opposite polarity of the second charge, or where the second charge has the opposite polarity of the first charge, and the third charge has the opposite polarity of the second charge.

2. The process of claim 1, wherein the generating step includes generating a first charge on the molecule where the molecule is selected from the group consisting of proteins, peptides, nucleic acids, oligonucleotides, oligosaccharides, and carbohydrates.

3. The process of claim 1, wherein the generating step includes generating a first charge on the molecule using a technique selected from the group consisting of plasma desorption ionization, field desorption ionization, electrohydrodynamic ionization, laser desorption ionization, matrix assisted laser desorption ionization, atmospheric pressure matrix assisted laser desorption ionization, electrospray ionization, nano-electrospray ionization, thermospray ionization, aerospray ionization, sonic spray ionization, fast atom bombardment, fast ion bombardment, secondary ion mass spectrometry, and massive cluster impact.

4. The process of claim 1, wherein the changing step includes changing the first charge to a second charge, where the absolute value of the second charge is equal to or less than the absolute value of the first charge.

5. The process of claim 1, wherein the changing step includes changing the first charge to a second charge, where the absolute value of the second charge is less than the absolute value of the first charge.

6. The process of claim 1, wherein the changing step includes changing the first charge to a second charge by contacting the molecule with a multiply charged ionic compound having a plurality of charged groups.

7. The process of claim 6, wherein plurality of charged groups is selected from the group consisting of ammonium groups, iminium groups, and protonated heteroaromatic groups.

8. The process of claim 7, wherein the changing step includes changing the first charge to a second charge by contacting the molecule with a multiply charged dendrimer.

9. The process of claim 6, wherein plurality of charged groups is selected from the group consisting of hydroxide groups, carboxylate groups, sulfonate groups, and phosphonate groups.

10. The process of claim 9, wherein the changing step includes changing the first charge to a second charge by contacting the molecule with a multiply charged dendrimer.

11. The process of claim 1, wherein the changing step includes changing the first charge to the second charge, where the molecule is in the gas phase.

12. The process of claim 1, wherein the changing step includes changing the first charge to a second charge in an ion storage trap selected from the group consisting of quadrupole ion traps and linear ion traps.

13. The process of claim 1, wherein the changing step includes changing the second charge to a third charge, where the absolute value of the third charge is equal to or greater than the absolute value of the second charge.

14. The process of claim 1, wherein the changing step includes changing the second charge to a third charge by contacting the molecule with a multiply charged ionic compound having a plurality of charged groups.

15. The process of claim 14, wherein the plurality of charged groups is selected from the group consisting of ammonium groups, iminium groups, and protonated heteroaromatic groups.

16. The process of claim 15, wherein the changing step includes changing the first charge to a second charge by contacting the molecule with a multiply charged dendrimer.

17. The process of claim 14, wherein the plurality of charged groups is selected from the group consisting of hydroxide groups, carboxylate groups, sulfonate groups, and phosphonate groups.

18. The process of claim 17, wherein the changing step includes changing the first charge to a second charge by contacting the molecule with a multiply charged dendrimer.

19. The process of claim 1, wherein the changing step includes changing the second charge to a third charge in an ion storage trap selected from the group consisting of quadrupole ion traps and linear ion traps.

20. The process of claim 1, wherein the changing step includes changing the second charge to a third charge, where the second charge is the opposite polarity of the third charge.

21. The process of claim 20, wherein the changing step includes changing the second charge to a third charge, where the second charge is a negative charge, by contacting the molecule with a compound selected from the group consisting of poly(alkyleneimine) dendrimers and poly(alkyleneamine) dendrimers.

22. The process of claim 20, wherein the changing step includes changing the second charge to the third charge, where the second charge is a positive charge, by contacting the molecule with a compound selected from the group consisting of poly(alkylenecarboxylic acid) dendrimers and poly(alkylenesulfonic acid) dendrimers.

23. The process of claim 1, further comprising the step of concentrating the third charge using ion parking.

24. The process of claim 1, further comprising detecting the molecule or a fragment thereof using tandem mass spectrometry.

25. The process of claim 24, further comprising concentrating the charge states of the molecule or a fragment thereof prior to the detecting step.

26. The process of claim 1, further comprising lowering the absolute value of the third charge by at least one using an atmospheric sampling glow discharge ionization source.

27. The process of claim 26, wherein the lowering step is performed prior to the detecting step.

28. The process of claim 1, further comprising identifying the molecule or a fragment thereof.

29. A process for analyzing a molecule by mass spectrometry, comprising:
(a) generating a first charge on the molecule;
(b) changing the first charge on the molecule to a second charge having the opposite polarity of the first charge; and
(c) changing the second charge on the molecule to a third charge having the opposite polarity of the second charge.

30. The process of claim 29, wherein the step of changing the first charge and the step of changing the second charge are performed contemporaneously, by contacting the molecule having the first charge, or a fragment thereof, with a first multiply charged ionic compound, and a second multiply charged ionic compound, where the first ionic compound and the second ionic compound have charges of opposite polarity.

31. A process for analyzing a molecule by mass spectrometry, comprising generating a first charge on the molecule having an absolute value equal to or greater than one; changing the first charge on the molecule to a second charge having an absolute value of one, by contacting the molecule with a first multiply charged ionic compound; and changing the second charge on the molecule to a third charge having an absolute value greater than one, by contacting the molecule with a second multiply charged ionic compound.

32. The process of claim 31, wherein the generating step includes generating the first charge by plasma desorption ionization, field desorption ionization, electrohydrodynamic ionization, laser desorption ionization, matrix assisted laser desorption ionization, atmospheric pressure matrix assisted laser desorption ionization, electrospray ionization, nanoelectrospray ionization, thermospray ionization, aerospray ionization, sonic spray ionization, fast atom bombardment, fast ion bombardment, secondary ion mass spectrometry, or massive cluster impact.

* * * * *